(12) United States Patent
Tamari et al.

(10) Patent No.: US 9,494,552 B2
(45) Date of Patent: Nov. 15, 2016

(54) METHOD AND SYSTEM FOR DOCUMENTING AN ELECTROPHORESIS GEL

(71) Applicant: Research Foundation of The City University of New York, New York, NY (US)

(72) Inventors: Farshad Tamari, Great Neck, NY (US); Farnaz Tamari, Great Neck, NY (US)

(73) Assignee: Research Foundation of The City University of New York, New York, NY (US)

(*) Notice: Subject to any disclaimer, the term of this patent is extended or adjusted under 35 U.S.C. 154(b) by 623 days.

(21) Appl. No.: 13/761,758

(22) Filed: Feb. 7, 2013

(65) Prior Publication Data

US 2013/0199930 A1 Aug. 8, 2013

Related U.S. Application Data

(60) Provisional application No. 61/596,162, filed on Feb. 7, 2012.

(51) Int. Cl.
*G01N 27/447* (2006.01)
(52) U.S. Cl.
CPC ................ *G01N 27/44704* (2013.01)
(58) Field of Classification Search
CPC .... G01N 27/44756–27/453; G01N 27/44721; B29C 39/00; B29C 39/06; B29C 39/22; B29C 39/26
See application file for complete search history.

(56) References Cited

U.S. PATENT DOCUMENTS

| 4,234,400 | A | * | 11/1980 | Kaplan et al. | 204/461 |
|---|---|---|---|---|---|
| 5,340,453 | A | * | 8/1994 | Jackson | 204/461 |
| 5,785,835 | A | * | 7/1998 | Saito et al. | 204/616 |
| 5,799,773 | A | * | 9/1998 | Heffelfinger et al. | 204/461 |
| 5,816,969 | A | | 10/1998 | Tsai | |
| 6,271,939 | B1 | | 8/2001 | Hu | |
| 2002/0134682 | A1 | * | 9/2002 | Chen | 204/621 |
| 2003/0015426 | A1 | * | 1/2003 | Rooney et al. | 204/467 |
| 2005/0023139 | A1 | * | 2/2005 | Rooney et al. | 204/450 |
| 2005/0127303 | A1 | * | 6/2005 | Waluszko | 250/374 |

OTHER PUBLICATIONS

Walter, W., "Buyer's Guide to Gel Documentation Systems," found on internet at: "http://www.the-scientist.com/?articles.view/articleNo/16715/title/Buyer-s-Guide-to-Gel-D . . . " as printed on Jan. 18, 2013, pp. 1 through 4.

* cited by examiner

*Primary Examiner* — Gurpreet Kaur
(74) *Attorney, Agent, or Firm* — Peter J. Mikesell; Schmeiser, Olsen & Watts, LLP (57) ABSTRACT

Disclosed in this specification is a high capacity compact gel documentation system for documenting different types of electrophoresis gels or other translucent objects using ultraviolet light. The system includes a base with a scanning surface having a transparent bottom surface. A light source is connected to a conveying mechanism, disposed below the transparent bottom surface, to move the light source over the length of the transparent bottom surface. An image capture device receives a reflected image and provides it to a microprocessor. Moreover, separate interchangeable filters allow for documentation of UV and white light gel captures, alleviating the need for separate transilluminators and hoods with filters and cameras.

16 Claims, 6 Drawing Sheets

METHOD AND SYSTEM FOR DOCUMENTING AN ELECTROPHORESIS GEL

CROSS-REFERENCE TO RELATED APPLICATIONS

This application claims priority to and the benefit of U.S. provisional patent application Ser. No. 61/596,162, filed Feb. 7, 2012, which application is incorporated herein by reference in its entirety.

FIELD OF THE INVENTION

This invention relates, in one embodiment, to gel documentation systems.

BACKGROUND

Gel documentation systems are used to record the image of an electrophoresis gel. In a conventional gel documentation system an electrophoresis gel is placed on an ultraviolet (UV) transilluminator. The UV transilluminator is often disposed proximate a relatively large hood to potentially entrapping harmful vapors that may be emitted from the gel and allow capture of images through creating a dark environment. Disposed above the gel is a light filter above which is placed digital camera. The transparent gel is illuminated with the transilluminator and an image of the illuminated gel is recorded with the digital camera. The UV transilluminator is used for ethidium bromide stained gels. Other gels require potentially a separate transilluminator, a separate hood with another filter and possibly a second camera.

Unfortunately, conventional gel documentation systems are expensive, typically costing over $30,000 each for a large, high-end system with more functionally and approximately $5,000 for a low end system with very limited capacity. Due to this expense, a given department often has only one such system. Therefore, an improved gel documentation system is desired.

SUMMARY OF THE INVENTION

Disclosed in this specification is a high capacity compact gel documentation system for documenting different types of electrophoresis gels or other translucent objects using ultraviolet light. The system includes a base with a scanning surface having a transparent bottom surface. A light source is connected to a conveying mechanism, disposed below the transparent bottom surface, to move the light source over the length of the transparent bottom surface. An image capture device receives a reflected image and provides it to a microprocessor. Moreover, separate interchangeable filters allow for documentation of UV and white light gel captures, alleviating the need for separate transilluminators and hoods with filters and cameras.

In one exemplary embodiment, a gel documentation system for documenting an electrophoresis gel is disclosed. The gel documentation system has an electrophoresis gel with a base that provides a transparent bottom surface. A light source is operatively connected to a conveying mechanism to move the light source over the length of the transparent bottom surface. The light source emits a narrowband wavelength of ultraviolet light.

In another exemplary embodiment, a gel documentation system for documenting an electrophoresis gel is disclosed. The gel documentation system has a cover and a base that provides a transparent bottom surface within a scanning recess. The scanning recess is disposed below a top surface of the base by a predetermined depth sufficient to contain an electrophoresis gel without the electrophoresis gel contacting the cover when the cover is disposed on the top surface of the base. A light source is operatively connected to a conveying mechanism to move the light source over the length of the transparent bottom surface. The light source emits a narrowband wavelength selected from the group consisting of 254 nm, 312 nm, 365 nm and combinations thereof.

In another exemplary embodiment, a method for documenting an electrophoresis gel is disclosed. The method includes the steps of disposing an electrophoresis gel within a scanning recess of a gel documentation system. The system includes a base with the scanning recess that provides a transparent bottom surface. The scanning recess is disposed below a top surface of the base by a predetermined depth sufficient to contain an electrophoresis gel without the electrophoresis gel contacting the cover when a cover is disposed on the top surface of the base. A light source is operatively connected to a conveying mechanism to move the light source over the length of the transparent bottom surface. The light source emits a narrowband wavelength selected from the group consisting of 254 nm, 312 nm, 365 nm and combinations thereof. The method further includes the steps of actuating the conveying mechanism to move the light source over at least a portion of the length of the transparent bottom surface and emitting light from the light source as the conveying mechanism is actuated. The method includes the step of capturing an image of the electrophoresis gel and digitizing the image.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
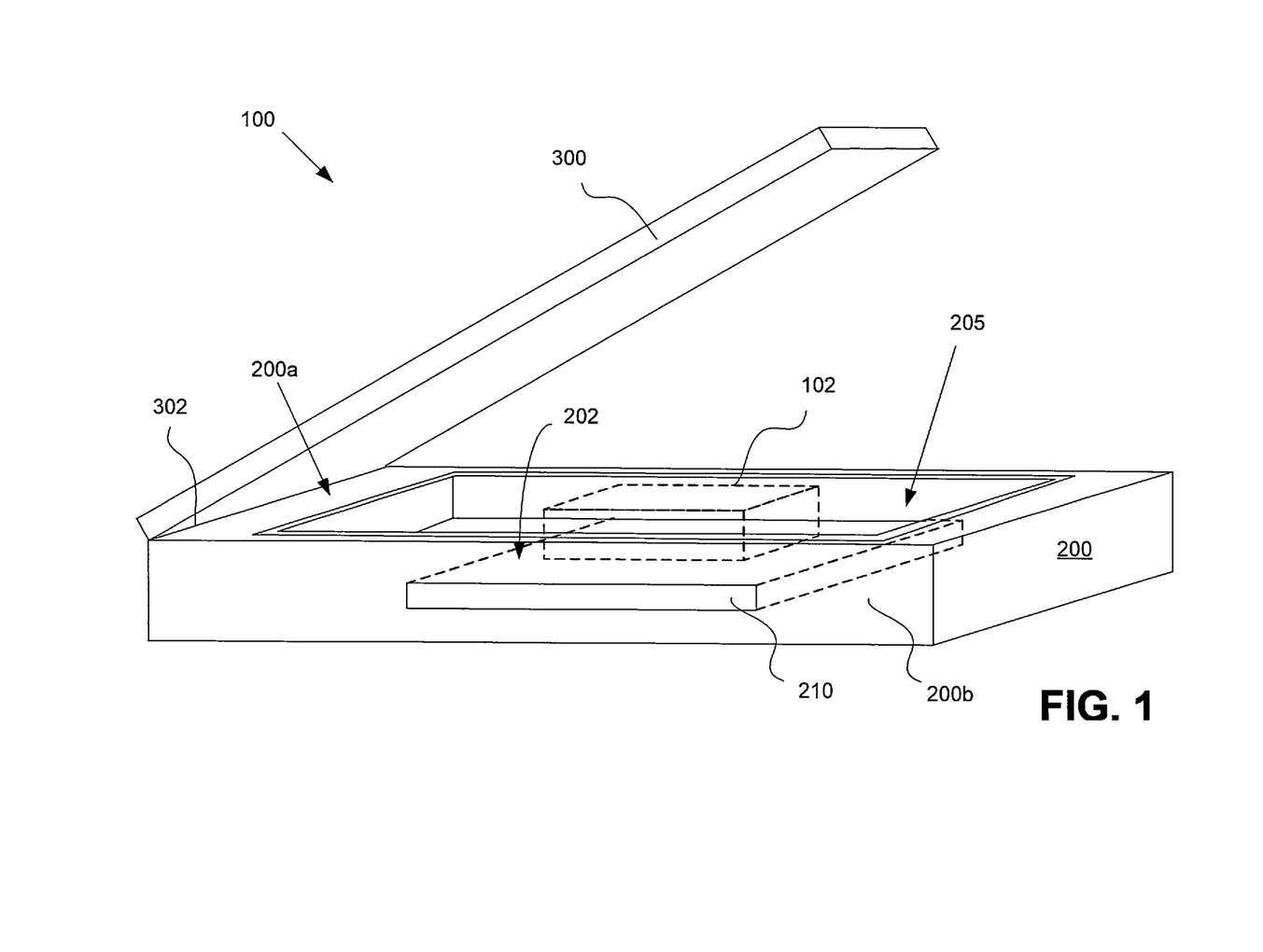
FIG. 1 is a perspective view of an exemplary gel documentation system.

FIG. 1 is a perspective view of an exemplary gel documentation system 100 for scanning an electrophoresis gel 102. System 100 comprises a base 200 with a scanning surface 202. The scanning surface 202 has a transparent bottom surface 203 (see FIG. 2A) with a length 206 and a width 208 (see FIG. 2B). The transparent bottom surface 203 is permeable to UV light and, in some embodiments, white light. The system 100 further comprises an exemplary cover 300 that is connected to an edge of the base 200 by a hinge 302. The base 200 may share many of the components of conventional flatbed scanners but the base 200 differs from such scanners as taught in the present specification.

Examples of conventional flatbed scanners include U.S. Pat. Nos. 5,816,969 and 6,271,939. The content of each of these patents is hereby incorporated by reference into this specification. A more detailed depiction of the base 200 is shown in FIG. 2A and FIG. 2B.

Figure 2A:
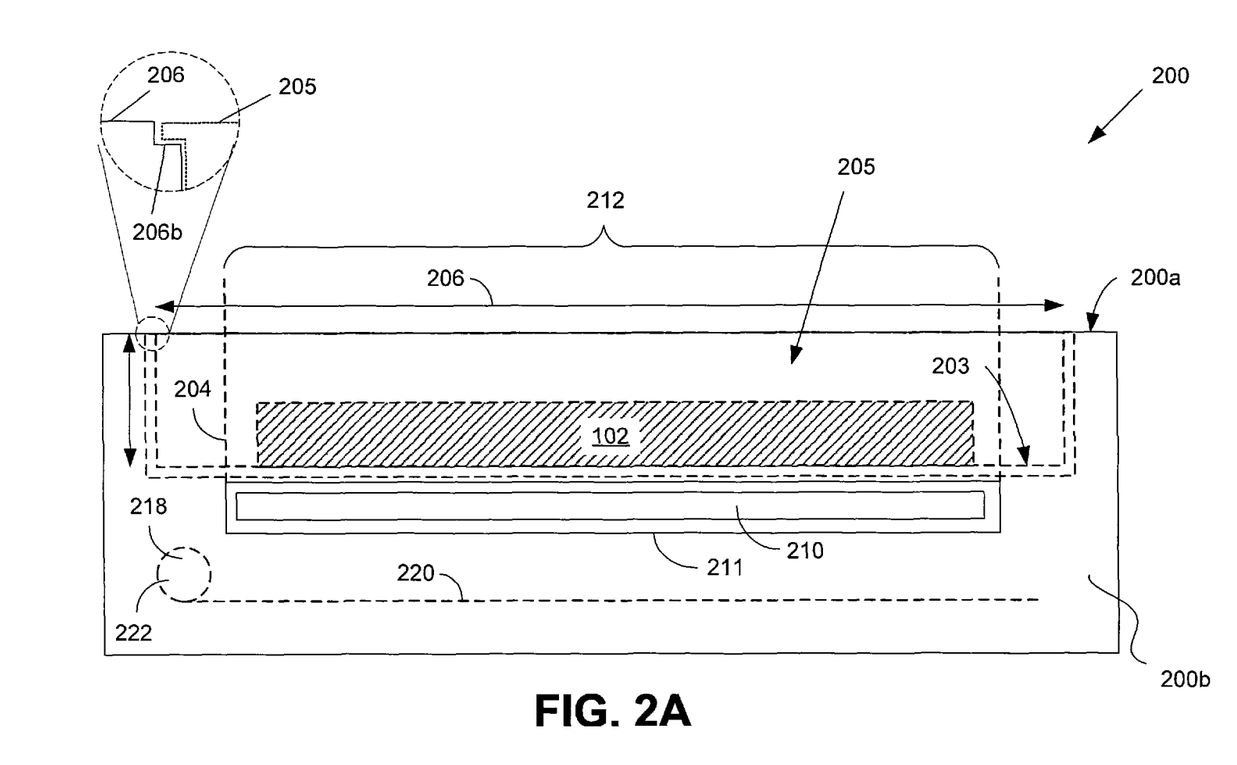
FIG. 2A is a cross sectional side view of an exemplary base.
Figure 2B:
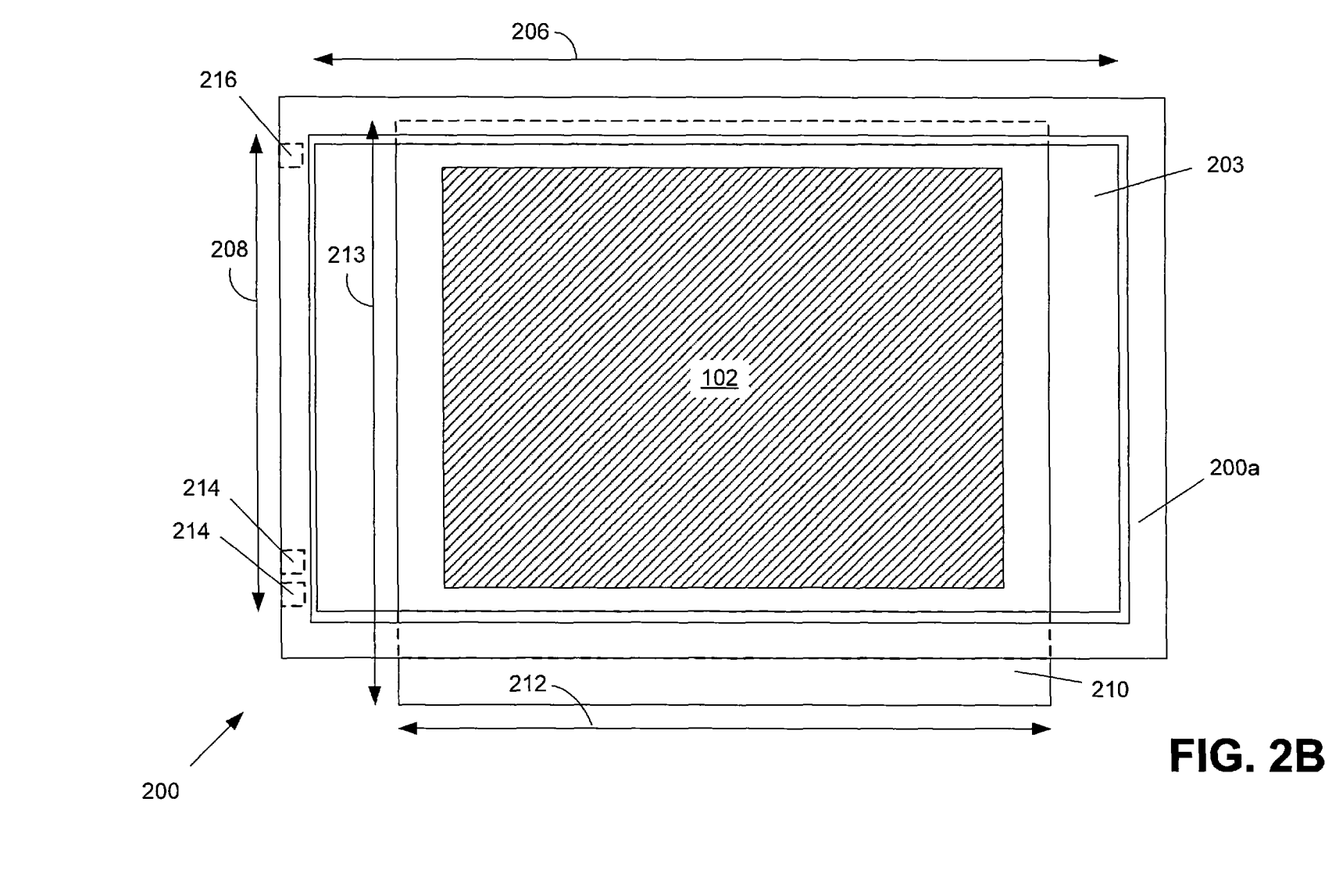
FIG. 2B is a top view of an exemplary base.

FIG. 2A is a cross sectional side view of the exemplary base 200. FIG. 2B is a top view of the exemplary base 200. In the exemplary embodiment, the scanning surface is a scanning recess 205 that provides a cavity to contain gel 102. The scanning recess 205 is disposed below a top surface 200a (see FIG. 1) of the base 200 by a predetermined depth 204. The depth 204 is selected to be greater than a height of the gel 102 thereby ensuring that, when the cover 300 is closed atop the base 200, the gel 102 is not touched by the cover 300. In another embodiment, not shown, the cover 300 includes a raised cavity that provides a recess to contain gel 102 to ensure the cover 300 does not touch the gel 102.

In one embodiment, the scanning recess 205 provides a liquid-tight tray that contains any residual moisture that may be excreted by the gel 102. In one embodiment, scanning recess 205 is a removable tray that rests on a ledge 206b proximate the top surface 200a of base 200. After use, the user need only lift the removable tray upwards to remove it from the base 200. The gel and any potentially hazardous chemicals associated with the gel may then be safely disposed in a conscientious manner. In one embodiment, the transparent bottom surface 203 and vertical sidewalls of the removable tray are discrete components joined by a liquid-tight seal. In another embodiment the transparent bottom surface 203 and vertical sidewalls are monolithic. In one such embodiment, a gentle slope is present between the transparent bottom surface 203 and vertical sidewalls to avoid the presence of a sharp corner that may prove difficult to clean.

The exemplary base 200 further comprises a slot 211 in a vertical edge 200b with a sliding filter 210 disposed therein. Sliding filter 210 is configured to filter light that passes therethrough. The slot 211 is positioned below the transparent bottom surface 203 of the scanning recess 205 and above a light source 218. The sliding filter 210 has a length 213 that is at least as long as the width 208 of the transparent bottom surface 203. The sliding filter 210 has a width 212 that is selected to be wider than the width of gel 102. In one embodiment, the sliding filter 210 has a length 213 and a width 212 sufficient to correspond to a portion of the area of the transparent bottom surface 203. In another embodiment, the sliding filter 210 has a length 213 and a width 212 sufficient to substantially correspond to the area of the transparent bottom surface 203. In the embodiment depicted, the slot 211 is disposed in a first edge such that the length of the sliding filter 210 traverses the width 208 of the transparent bottom surface 203. Because the sliding filter 210 is removable from the slot 211, different filters 210 may be interchangeably inserted into the slot 211.

The light source 218 is operatively connected to a conveying mechanism 220 that is configured to move the light source 218 over at least a portion of the length 212 of the scanning recess 205. The conveying mechanism 220 may include a means for driving the light source 218 past the object being documented. Examples of suitable means for driving include a stepper motor. In one embodiment, the light source 218 is configured to emit ultraviolet (UV) light and white light. In another embodiment, the light source 218 is configured to emit only white light. In another embodiment, the light source 218 is configured to emit only ultraviolet light. In yet another embodiment, the light source 218 is configured to emit only ultraviolet light at a predetermined wavelength selected from 254 nm, 312 nm, 365 nm or combinations thereof. In some embodiments, the wavelength of light is controlled such that only a narrow bandwidth of less than about 10 nm is emitted. The base 200 also comprises an image capture device 222 which, in the depicted embodiment, is disposed on the conveying mechanism to receive a reflected image of the gel 102 when the gel 102 is illuminated by light source 218. Examples of suitable image capture devices 222 include an array of photodiodes including a charge-coupled device (CCD). The image capture device 222 may further include an analog-to-digital converter.

The base 200 may also include a power input 216 which may connect to an external power supply. In another embodiment, the base 200 includes a battery, such as a backup battery. One or more data ports 214 may also be provided. The data ports 214 permit the system 100 to be in wired or wireless communication with external devices (e.g. printers, computers, data storage devices including hard drives, flash drives, and the like). In one embodiment, at least one of the data ports 214 is a Universal Serial Bus (USB) data port. In this fashion digital images of the gel 102 may be printed and/or saved to an external device for further manipulation. In one embodiment, the base 200 includes a built-in printer.

Figure 3:
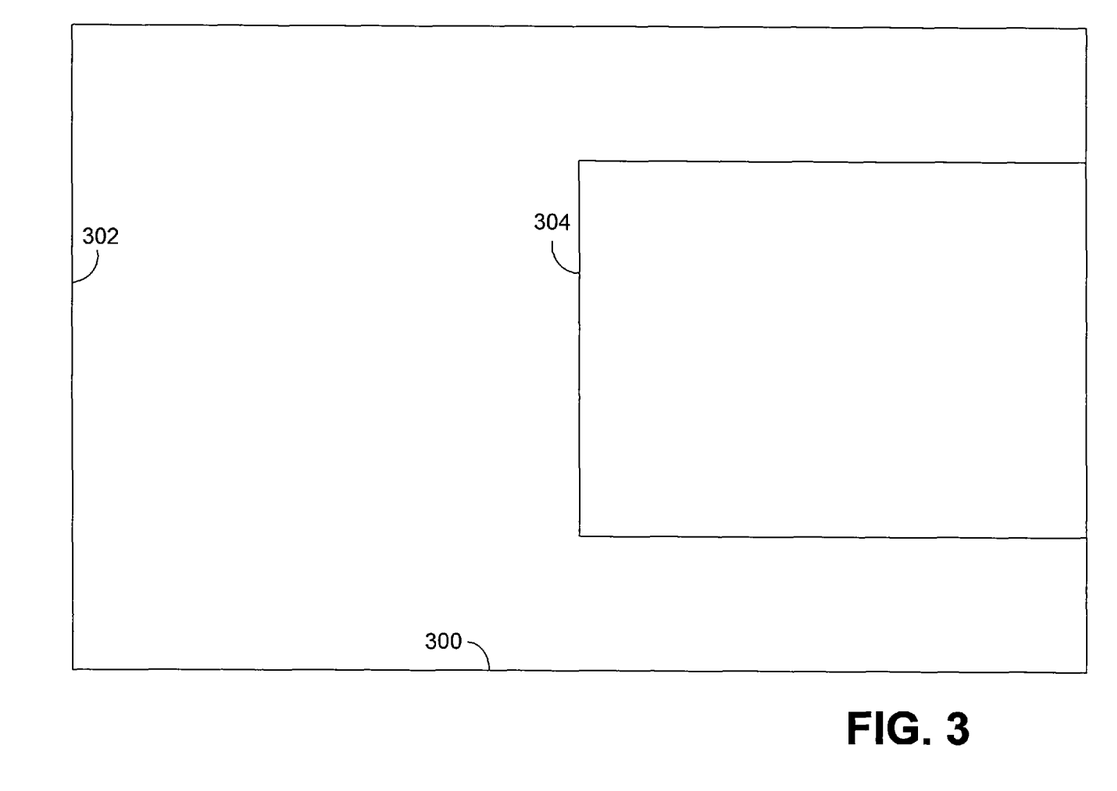
FIG. 3 is a top view of an exemplary cover.

FIG. 3 is a top view of the exemplary cover 300. The cover 300 comprises a display 304 that is operatively connected to a microprocessor to provide a user interface. In one embodiment, display 304 is a touch screen display. Display 304 may be configured to provide a preview image of the gel 102 as the documentation method occurs. In this fashion a user is permitted to rapidly see the results of the current documentation attempt and, if desired, adjust the system in an attempt to obtain a better image. Display 304, in certain embodiments, provides a mechanism for permitting the user to navigate through software menus to select certain features. Examples of such features include copying of digital files to an attached storage device, printing to an attached or integral printer, and the like.

Figure 4:
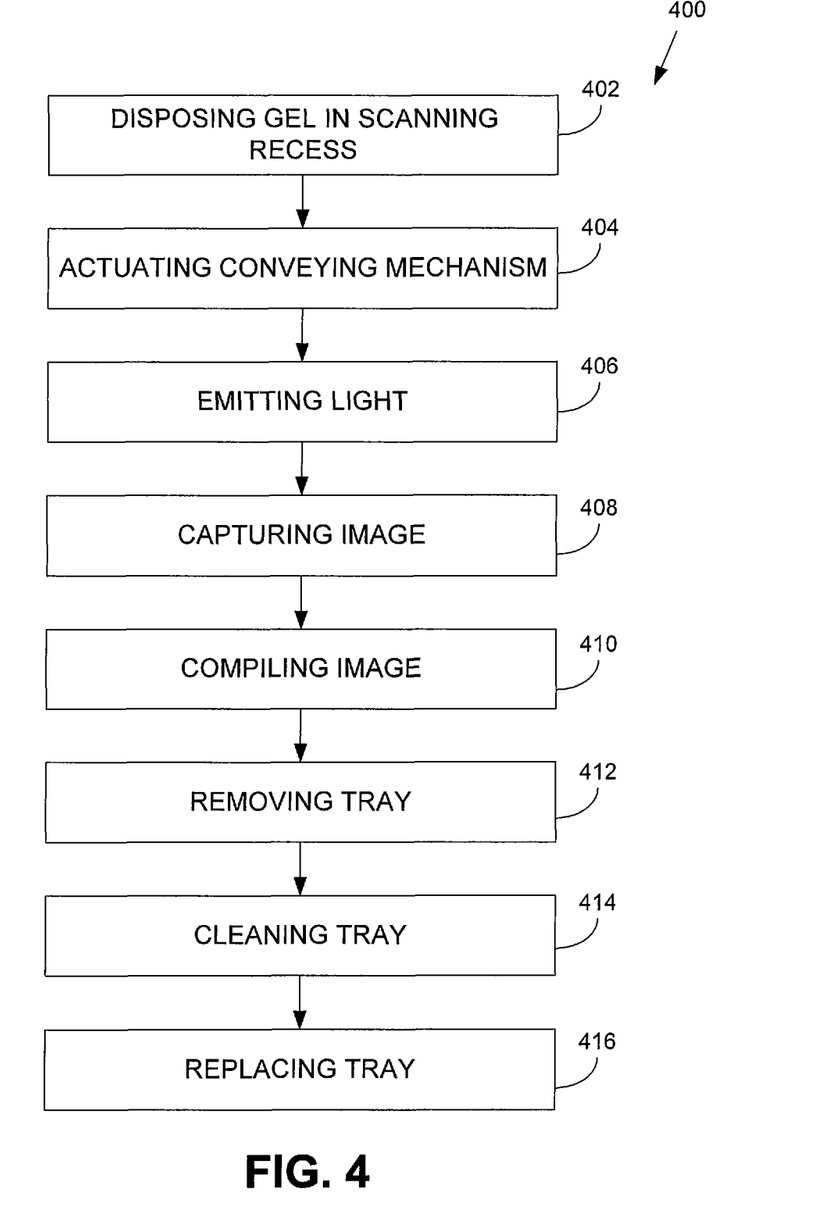
FIG. 4 is a flow diagram depicting an exemplary method for documenting an electrophoresis gel.
Figure 5:
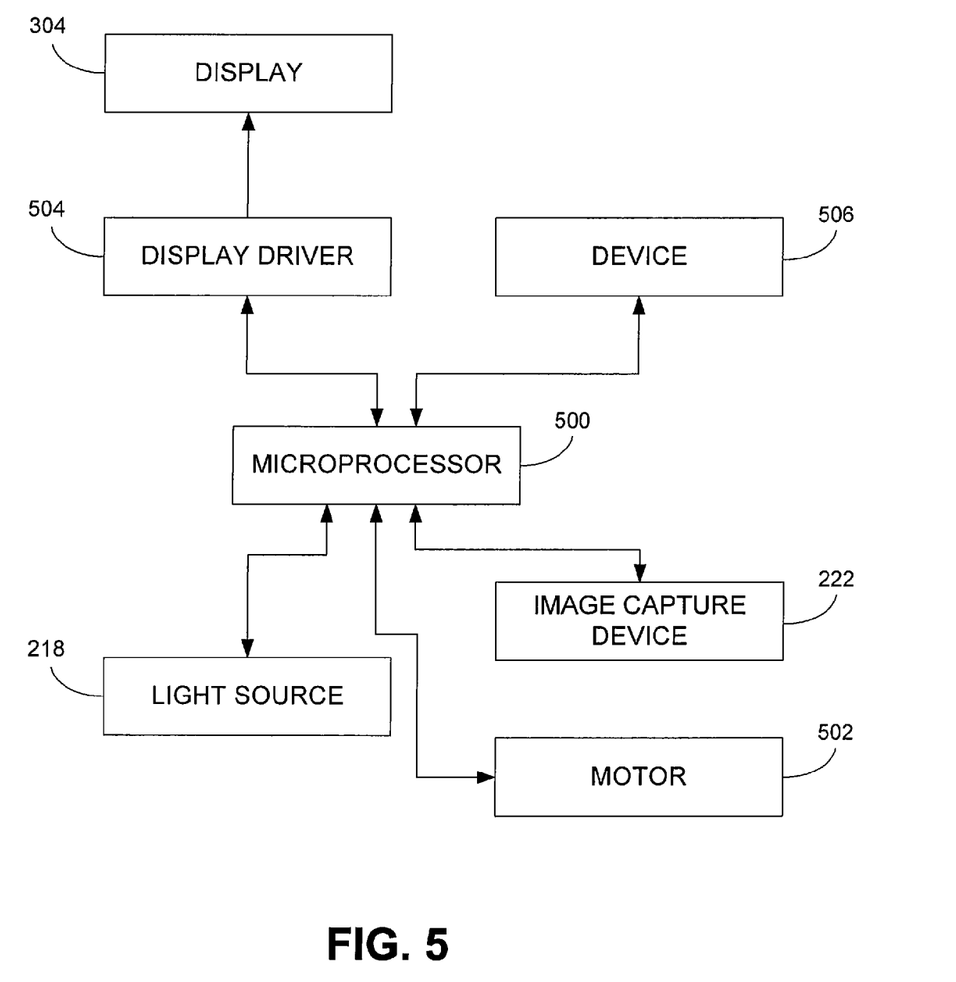
FIG. 5 is a block diagram of select components of a gel documentation system.

FIG. 4 is a flow diagram depicting an exemplary method 400 for documenting an electrophoresis gel. The method will be further described with reference to FIG. 5 which is a block diagram of select components of a gel documentation system. As shown in FIG. 5 a microprocessor 500 controls various components of the gel documentation system including the light source 218 and the image capture device 222. The microprocessor 500 also controls motor 502 which, in one embodiment, is a stepper motor of the conveying mechanism 220. The microprocessor is also in communication with a display driver 504 which controls display 304. Devices 506, such as internal memory devices or external devices, are also in communication with microprocessor 500. The method 400 begins with a step 402.

Referring again to FIG. 4, in step 402 a gel 102 is disposed in the scanning recess 205 of the gel documentation system 100. The cover 300 may be closed to provide a light controlled (e.g. dark) environment within the scanning recess 205. The light-controlled environment also contains ultraviolet light from the light source 218 which provides a safety benefit to the user. In step 404 the conveying mechanism 220 is actuated. For example, the display 304 may include a "scan" graphic that performs the actuation. Upon actuation, the microprocessor 500 controls the motor 502 of the conveying mechanism 220. This, in turn, causes the light source 218 and the image capture device 222 to traverse past the object being scanned. During movement, the microprocessor 500 activates the light source 218 and receives data from the image capture device 222. When the conveying mechanism 220 reaches a predetermined position, the light source 218 and the image capture device 222 are deactivated and the conveying mechanism 220 is returned to its original position. The data received from the image capture device is then processed into a digital image. For example, current and/or voltage data from an array of photodiodes in the image capture device 222 is sent to an analog-to-digital converter. The resulting digital signals are representative of the captured image. The digital signals are then sent, by the microprocessor 500, to a display driver 504. The display driver 504 applies digital signals to the display 304 to generate an image representative of the captured image.

In step 406, light is emitted from the light source 218 as the conveying mechanism 220 moves it across the length 206 of the scanning recess 205. The reflected light is received by the image capture device 222 in step 408. The captured image is received in sequential slices as the conveying mechanism 220 moves. Each slice is provided to a microprocessor within the base 200 and the microprocessor compiles the slices into a compiled digital image of the gel 102 in step 410. The compiled image is displayed to the user on display 304 and the user then determines whether or not the image should be saved to a storage medium.

In some embodiments, the scanning recess 205 is then removed from the base in step 412. In step 414 the gel 102 is disposed and the scanning recess 205 is cleaned. In step 416 the scanning recess 205 is replaced into the base 200 for subsequent use.

In one embodiment, the system 100 includes a means to select the wavelength of light that is emitted from the light source 218. In one embodiment, the display 304 is a touch screen display and the means to select the wavelength is the touch screen display. In another embodiment, the means to select the wavelength is one or more switches on the base. In one embodiment, the user may select, for example, wavelengths of 324 nm, 312 nm, 365 nm, and any combination thereof, or white light.

The conveying mechanism 220 provides a mechanism to control the exposure time of the gel 102. Convention gel documentation systems can only control exposure time by leaving the camera open for a predetermined period of time. With conventional systems, this necessarily requires all section of the gel be imaged with equal light intensity. In contrast, the conveying mechanism 220 can be adjusted to control the exposure time of the gel 102. For example, in one embodiment, an initial digital image is compiled at a relatively fast conveying speed. The user can see a preview image of the gel 102 at this fast speed in display 302. After the preview image is deemed satisfactory, a subsequent image can be acquired at slower conveying speed with a longer exposure time.

The gel documentation system described herein is substantially more compact and inexpensive than previous systems to provide a new system that requires minimal training and is easy to use. Although the exemplary embodiments described herein have focused on electrophoresis gels the system is also applicable to other translucent objects.

While the invention has been described with reference to certain embodiments, it will be understood by those skilled in the art that various changes may be made and equivalents may be substituted for elements thereof to adapt to particular situations without departing from the scope of the disclosure. Therefore, it is intended that the claims not be limited to the particular embodiments disclosed, but that the claims will include all embodiments falling within the scope and spirit of the appended claims.

What is claimed is:

1. A gel documentation system for documenting an electrophoresis gel, the system comprising:
   a base with a scanning surface comprising a transparent bottom surface with a length and a width;
   a light source operatively connected to a conveying mechanism to move the light source over the length of the transparent bottom surface, the conveying mechanism being disposed below the transparent bottom surface, wherein the light source emits a narrowband wavelength of ultraviolet light;
   an image capture device for receiving a reflected image;
   a microprocessor operatively connected to the image capture device, wherein the base comprises a slot and a sliding filter is inserted into the slot such that the sliding filter is disposed between the light source and the transparent bottom surface;
   wherein the sliding filter has a length that is greater than the width of the transparent bottom surface;
   wherein the slot is disposed in a first edge such that the length of the sliding filter extends perpendicular to the length of the transparent bottom surface.

2. The gel documentation system as recited in claim 1 wherein the light source emits a narrowband wavelength of 254 nm.

3. The gel documentation system as recited in claim 1 wherein the narrowband wavelength of ultraviolet light is selected from the group consisting of 254 nm, 312 nm, 365 nm and combinations thereof.

4. A gel documentation system for documenting an electrophoresis gel, the system comprising:
   a base with a scanning surface comprising a transparent bottom surface with a length and a width;
   a cover connected to the base with a hinge;
   a light source operatively connected to a conveying mechanism to move the light source over the length of the transparent bottom surface, the conveying mechanism being disposed below the transparent bottom surface, wherein the light source emits a narrowband wavelength of ultraviolet light;
   an image capture device for receiving a reflected image;
   a microprocessor operatively connected to the image capture device, the cover having a touch screen display operatively connected to the microprocessor.

5. A gel documentation system for documenting an electrophoresis gel, the system comprising:
   a cover;
   a base with a scanning recess comprising a transparent bottom surface with a length and a width, the scanning recess being disposed below a top surface of the base by a predetermined depth sufficient to contain an electrophoresis gel without the electrophoresis gel contacting the cover when the cover is disposed on the top surface of the base;
   a light source operatively connected to a conveying mechanism to move the light source over the length of the transparent bottom surface, the conveying mechanism being disposed below the transparent bottom surface, wherein the light source emits a narrowband wavelength selected from the group consisting of 254 nm, 312 nm, 365 nm and combinations thereof;
   an image capture device for receiving a reflected image, the image capture device comprising means for converting the reflected image into digital signals representative of the reflected image;

a microprocessor operatively connected to the image capture device, the cover having a touch screen display operatively connected to the microprocessor.

6. The gel documentation system as recited in claim 5, wherein the scanning recess is a removable tray with vertical sidewalls that define the predetermined depth.

7. The gel documentation system as recited in claim 6, wherein the predetermined depth is at least about 0.5 cm.

8. The gel documentation system as recited in claim 6, wherein the predetermined depth is at least about 1 cm.

9. The gel documentation system as recited in claim 6, wherein the light source emits a narrowband wavelength of 254 nm.

10. A method for documenting an electrophoresis gel, the method comprising the steps of:
  disposing an electrophoresis gel within a scanning recess of a gel documentation system, the system comprising:
    a cover;
    a base with the scanning recess comprising a transparent bottom surface with a length and a width, the scanning recess being disposed below a top surface of the base by a predetermined depth sufficient to contain an electrophoresis gel without the electrophoresis gel contacting the cover when the cover is disposed on the top surface of the base;
    a light source operatively connected to a conveying mechanism to move the light source over the length of the transparent bottom surface, the conveying mechanism being disposed below the transparent bottom surface;
    an image capture device for receiving a reflected image;
    a microprocessor operatively connected to the image capture device, the cover having a touch screen display operatively connected to the microprocessor;
  actuating the conveying mechanism to move the light source over at least a portion of the length of the transparent bottom surface;
  emitting light from the light source as the conveying mechanism is actuated;
  capturing an image of the electrophoresis gel with the image capture device;
  digitizing the image using the microprocessor.

11. The method as recited in claim 10, wherein the step of emitting light emits white light.

12. The method as recited in claim 10, wherein the step of emitting light emits a narrowband wavelength selected from the group consisting of 254 nm, 312 nm, 365 nm and combinations thereof.

13. The method as recited in claim 10, wherein the step of emitting light emits a narrowband wavelength of 254 nm.

14. The method as recited in claim 10, wherein the step of capturing the image compiles the image by sequentially capturing image slices during the step of actuating the conveying mechanism.

15. The method as recited in claim 10, the method further comprising
  removing the scanning recess from the base after the step of capturing;
  cleaning the scanning recess after the step of removing; and
  replacing the scanning recess after the step of cleaning.

16. The method as recited in claim 15, wherein the step of replacing hangs the scanning recess on a ledge that is proximate the top surface of the base.

* * * * *